(12) United States Patent
Bacon (10) Patent No.: US 8,408,208 B2
(45) Date of Patent: Apr. 2, 2013

(54) DISPENSER AND COUNTER

(75) Inventor: Raymond John Bacon, Petersfield (GB)

(73) Assignee: Clinical Designs Limited, Hampshire (GB)

( * ) Notice: Subject to any disclaimer, the term of this patent is extended or adjusted under 35 U.S.C. 154(b) by 705 days.

(21) Appl. No.: 10/582,656

(22) PCT Filed: Dec. 10, 2004

(86) PCT No.: PCT/GB2004/005165
§ 371 (c)(1),
(2), (4) Date: Apr. 3, 2007

(87) PCT Pub. No.: WO2005/056090
PCT Pub. Date: Jun. 23, 2005

(65) Prior Publication Data
US 2007/0251950 A1 Nov. 1, 2007

(30) Foreign Application Priority Data
Dec. 12, 2003 (GB) .................................. 0328859.4

(51) Int. Cl.
*A62B 7/00* (2006.01)
*A62B 9/00* (2006.01)
*B67D 7/22* (2010.01)
*G09F 9/00* (2006.01)

(52) U.S. Cl. ......... 128/205.23; 128/200.23; 128/200.14; 128/200.21; 128/203.12; 128/200.15; 128/204.18; 222/36; 222/325; 222/402.13; 222/38; 222/32; 222/162; 222/23; 222/29; 221/8; 116/307; 116/309; 116/312; 116/313; 116/284

(58) Field of Classification Search ............. 128/200.23, 128/200.14, 205.23, 200.21, 203.12, 200.15, 128/204.18; 222/36, 325, 402.13, 38, 32, 222/162, 23, 29; 116/307, 309, 312, 313, 116/284; 221/8
See application file for complete search history.

(56) References Cited

U.S. PATENT DOCUMENTS

| 2,002,835 A | 5/1935 | Rose |
| 2,716,013 A | 8/1955 | Tinker |
| 2,773,631 A | 12/1956 | Bryant |
| 2,922,613 A | 1/1960 | Beacham et al. |
| 2,974,835 A | 3/1961 | Herbrick |

(Continued)

FOREIGN PATENT DOCUMENTS

| AU | 776816 | 7/2002 |
| AU | 2003234746 | 9/2003 |

(Continued)

*Primary Examiner* — Gene O. Crawford
*Assistant Examiner* — Rakesh Kumar
(74) *Attorney, Agent, or Firm* — Ware, Fressola, Maguire & Barber, LLP (57) ABSTRACT

The dispenser has a body (1), with a mouthpiece cover (2). Opening of the cover urges a junction member (3) towards a source (4) of a medicament to be released as a dose by pressing a spout (5) of the source inwards of the source. The source is supported by a cap (11) clipped to the end of a source-enclosing barrel (12) with internal splines (10). The barrel is welded (15) to the main to part (16) of the body at a position determined by the extension of the source towards the distal end (17) of the barrel when the cover is open, the welding position being determined by a plug (18) simulating the cap and its bush.

36 Claims, 8 Drawing Sheets

U.S. PATENT DOCUMENTS

| | | | |
|---|---|---|---|
| 3,012,454 A | 12/1961 | Brodbeck | |
| 3,103,335 A | 9/1963 | Martinez | |
| 3,181,743 A | 5/1965 | Libit et al. | |
| 3,187,748 A | 6/1965 | Mitchell et al. | |
| 3,190,497 A | 6/1965 | Anthon | |
| 3,294,293 A | 12/1966 | Johns | |
| 3,305,144 A | 2/1967 | Beres et al. | |
| 3,329,389 A | 7/1967 | Clark | |
| 3,395,838 A | 8/1968 | Beres et al. | |
| 3,439,846 A | 4/1969 | Evras | |
| 3,456,646 A | 7/1969 | Phillips et al. | |
| 3,789,943 A | 2/1974 | Kampert et al. | |
| 3,913,882 A | 10/1975 | Moulet | |
| 3,926,339 A | 12/1975 | Openchowski | |
| 3,926,347 A | 12/1975 | Low et al. | |
| 3,927,484 A * | 12/1975 | Spiegel et al. | 40/307 |
| 4,085,886 A | 4/1978 | Nishioka | |
| 4,109,836 A | 8/1978 | Falarde | |
| 4,142,651 A | 3/1979 | Leopoldi et al. | |
| 4,354,660 A | 10/1982 | Stupar et al. | |
| 4,414,972 A | 11/1983 | Young et al. | |
| 4,457,699 A | 7/1984 | Hattori | |
| 4,538,740 A * | 9/1985 | Petersen, Jr. | 215/246 |
| 4,570,898 A | 2/1986 | Staeubli | |
| 4,576,157 A | 3/1986 | Raghuprasad | |
| 4,664,107 A | 5/1987 | Wass | |
| 4,703,761 A | 11/1987 | Rathbone et al. | |
| 4,707,038 A | 11/1987 | Voegeli | |
| 4,803,978 A | 2/1989 | Johnson, IV et al. | |
| 4,817,822 A | 4/1989 | Rand et al. | |
| 4,819,834 A | 4/1989 | Thiel | |
| 4,863,379 A | 9/1989 | Timerdahl et al. | |
| 4,955,371 A | 9/1990 | Zamba et al. | |
| 4,969,578 A * | 11/1990 | Gander et al. | 222/131 |
| 4,972,830 A | 11/1990 | Wong et al. | |
| 4,984,158 A | 1/1991 | Hillsman | |
| 5,020,527 A * | 6/1991 | Dessertine | 128/200.23 |
| 5,031,610 A | 7/1991 | Armstrong et al. | |
| 5,042,526 A | 8/1991 | Kulakoff | |
| 5,042,685 A | 8/1991 | Moulding, Jr. et al. | |
| 5,060,643 A * | 10/1991 | Rich et al. | 128/200.23 |
| 5,069,204 A | 12/1991 | Smith et al. | |
| 5,113,855 A | 5/1992 | Newhouse | |
| 5,119,806 A | 6/1992 | Palson et al. | |
| 5,152,456 A | 10/1992 | Ross et al. | |
| 5,184,761 A | 2/1993 | Lee | |
| 5,193,745 A | 3/1993 | Holm | |
| 5,217,004 A | 6/1993 | Blasnik et al. | |
| 5,224,472 A | 7/1993 | Pesenti et al. | |
| 5,239,992 A | 8/1993 | Bougamont et al. | |
| 5,273,172 A | 12/1993 | Rossbach et al. | |
| 5,295,479 A | 3/1994 | Lankinen | |
| 5,297,542 A | 3/1994 | Bacon | |
| 5,299,701 A | 4/1994 | Barker et al. | |
| 5,347,998 A | 9/1994 | Hodson et al. | |
| 5,370,279 A | 12/1994 | Tardif | |
| 5,388,572 A | 2/1995 | Mulhauser et al. | |
| 5,402,823 A | 4/1995 | Cole | |
| 5,408,994 A | 4/1995 | Wass et al. | |
| 5,415,161 A | 5/1995 | Ryder | |
| 5,421,482 A | 6/1995 | Garby et al. | |
| 5,447,150 A | 9/1995 | Bacon | |
| 5,469,843 A | 11/1995 | Hodson | |
| 5,482,030 A * | 1/1996 | Klein | 128/200.23 |
| 5,487,378 A | 1/1996 | Robertson et al. | |
| 5,501,375 A | 3/1996 | Nilson | |
| 5,505,192 A * | 4/1996 | Samiotes et al. | 128/200.14 |
| 5,511,540 A | 4/1996 | Bryant et al. | |
| 5,544,647 A | 8/1996 | Jewett et al. | |
| 5,544,657 A | 8/1996 | Kurowski et al. | |
| 5,546,932 A | 8/1996 | Galli | |
| 5,549,101 A | 8/1996 | Trofast et al. | |
| 5,549,226 A | 8/1996 | Kopp | |
| 5,564,414 A | 10/1996 | Walker et al. | |
| 5,611,444 A | 3/1997 | Garby et al. | |
| 5,622,163 A | 4/1997 | Jewett et al. | |
| 5,623,920 A | 4/1997 | Bryant | |
| 5,645,050 A | 7/1997 | Zierenberg et al. | |
| 5,655,523 A | 8/1997 | Hodson et al. | |
| 5,667,142 A | 9/1997 | Newman | |
| 5,669,376 A * | 9/1997 | Sioutas | 128/200.23 |
| 5,692,492 A | 12/1997 | Bruna et al. | |
| 5,707,038 A | 1/1998 | Cocatre-Zilgien | |
| 5,718,355 A | 2/1998 | Garby et al. | |
| 5,740,793 A | 4/1998 | Hodson et al. | |
| 5,772,085 A | 6/1998 | Bryant et al. | |
| 5,785,209 A * | 7/1998 | Guglielmini | 222/153.07 |
| 5,794,612 A | 8/1998 | Watcher et al. | |
| 5,799,651 A * | 9/1998 | Garby et al. | 128/200.23 |
| 5,809,997 A | 9/1998 | Wolf | |
| 5,839,429 A | 11/1998 | Marnfeldt et al. | |
| 5,988,496 A | 11/1999 | Bruna | |
| 5,996,577 A | 12/1999 | Ohki et al. | |
| 6,029,659 A * | 2/2000 | O'Connor | 128/203.12 |
| 6,085,742 A | 7/2000 | Wachter et al. | |
| 6,148,815 A | 11/2000 | Wolf | |
| 6,149,054 A | 11/2000 | Cirrillo et al. | |
| 6,152,130 A | 11/2000 | Abrams et al. | |
| 6,155,251 A * | 12/2000 | Hauser | 128/200.23 |
| 6,202,642 B1 | 3/2001 | McKinnon et al. | |
| 6,205,999 B1 | 3/2001 | Ivri et al. | |
| 6,234,168 B1 | 5/2001 | Bruna | |
| 6,240,918 B1 | 6/2001 | Ambrosio et al. | |
| 6,260,549 B1 | 7/2001 | Sosiak | |
| 6,283,365 B1 | 9/2001 | Bason | |
| 6,336,453 B1 | 1/2002 | Scarrott et al. | |
| 6,354,290 B1 | 3/2002 | Howlett | |
| 6,357,442 B1 | 3/2002 | Casper et al. | |
| 6,397,839 B1 | 6/2002 | Stradella | |
| 6,405,727 B1 | 6/2002 | MacMichael et al. | |
| 6,415,784 B1 | 7/2002 | Christrup et al. | |
| 6,419,101 B1 * | 7/2002 | Hessel et al. | 215/253 |
| 6,422,234 B1 | 7/2002 | Bacon | |
| 6,427,683 B1 | 8/2002 | Drachmann et al. | |
| 6,431,168 B1 | 8/2002 | Rand et al. | |
| 6,439,227 B1 | 8/2002 | Myrman et al. | |
| 6,442,234 B1 | 8/2002 | Morken et al. | |
| 6,443,146 B1 | 9/2002 | Voges | |
| 6,460,537 B1 | 10/2002 | Bryant et al. | |
| 6,470,884 B2 * | 10/2002 | Horlin | 128/203.15 |
| 6,510,847 B1 | 1/2003 | Helgesson et al. | |
| 6,553,988 B1 * | 4/2003 | Holroyd | 128/200.23 |
| 6,581,590 B1 | 6/2003 | Genova et al. | |
| 6,601,582 B2 | 8/2003 | Rand et al. | |
| 6,615,827 B2 | 9/2003 | Greenwood et al. | |
| 6,637,432 B2 | 10/2003 | Wakefield et al. | |
| 6,655,379 B2 | 12/2003 | Clark et al. | |
| 6,659,307 B1 | 12/2003 | Stradella | |
| 6,672,304 B1 | 1/2004 | Casper et al. | |
| 6,752,145 B1 | 6/2004 | Bonney et al. | |
| 6,755,190 B2 | 6/2004 | Rasmussen | |
| 6,866,037 B1 | 3/2005 | Aslin et al. | |
| 6,907,876 B1 | 6/2005 | Clark et al. | |
| 6,926,002 B2 | 8/2005 | Scarrott et al. | |
| 6,981,602 B2 * | 1/2006 | Ma et al. | 215/254 |
| 7,036,505 B2 | 5/2006 | Bacon et al. | |
| 7,047,964 B2 * | 5/2006 | Bacon | 128/200.23 |
| 7,093,594 B2 | 8/2006 | Harrison et al. | |
| 7,100,530 B2 * | 9/2006 | Lu | 116/307 |
| 7,107,986 B2 | 9/2006 | Rand et al. | |
| 7,191,918 B2 | 3/2007 | Ouyang et al. | |
| 7,195,134 B2 | 3/2007 | Ouyang et al. | |
| 7,270,124 B2 | 9/2007 | Rasmussen | |
| 7,341,057 B2 | 3/2008 | Scarrott et al. | |
| 7,387,121 B2 | 6/2008 | Harvey | |
| 7,454,267 B2 | 11/2008 | Bonney et al. | |
| 7,584,712 B2 * | 9/2009 | Lu | 116/307 |
| 7,597,099 B2 | 10/2009 | Jones et al. | |
| 7,621,273 B2 * | 11/2009 | Morton et al. | 128/205.23 |
| 7,814,900 B2 * | 10/2010 | Bacon | 128/200.14 |
| 2001/0013343 A1 | 8/2001 | Andersson | |
| 2002/0000225 A1 | 1/2002 | Schuler et al. | |
| 2002/0047021 A1 | 4/2002 | Blacker et al. | |
| 2002/0056449 A1 | 5/2002 | Wakefield et al. | |
| 2002/0139812 A1 | 10/2002 | Scarrott et al. | |
| 2002/0153005 A1 * | 10/2002 | Scarrott et al. | 128/200.14 |
| 2002/0195102 A1 | 12/2002 | Rand et al. | |

| | | | | | |
|---|---|---|---|---|---|
| 2003/0089368 A1 | 5/2003 | Zhao | GB | 2079183 | 1/1982 |
| 2003/0136401 A1 | 7/2003 | Jansen et al. | GB | 2191032 | 12/1987 |
| 2003/0183226 A1 | 10/2003 | Brand et al. | GB | 2233236 | 1/1991 |
| 2004/0025868 A1 | 2/2004 | Bruna | GB | 2262452 | 6/1993 |
| 2004/0069301 A1* | 4/2004 | Bacon ............... 128/200.23 | GB | 2263873 | 8/1993 |
| 2004/0089299 A1 | 5/2004 | Bonney et al. | GB | 2264238 | 8/1993 |
| 2004/0134488 A1 | 7/2004 | Davies | GB | 2266466 | 11/1993 |
| 2004/0144798 A1 | 7/2004 | Ouyang et al. | GB | 2279571 | 1/1995 |
| 2004/0149773 A1* | 8/2004 | Ouyang et al. ............. 222/36 | GB | 2279879 | 1/1995 |
| 2004/0221840 A1* | 11/2004 | Stockman-Lamb ..... 128/200.23 | GB | 2292891 | 3/1996 |
| 2005/0087191 A1* | 4/2005 | Morton et al. ........... 128/205.23 | GB | 2320489 | 6/1998 |
| 2005/0205512 A1 | 9/2005 | Scarrott et al. | GB | 2366519 | 3/2002 |
| 2005/0209558 A1 | 9/2005 | Marx | GB | 2372542 | 8/2002 |
| 2006/0231093 A1 | 10/2006 | Burge et al. | GB | 2385640 | 8/2003 |
| 2006/0278225 A1 | 12/2006 | MacMichael et al. | HU | 67279 | 3/1995 |
| 2007/0062518 A1 | 3/2007 | Geser et al. | JP | 63251880 | 10/1988 |
| 2007/0089735 A1 | 4/2007 | Langfor et al. | JP | 06027550 | 4/1994 |
| 2008/0066750 A1 | 3/2008 | Minshull et al. | JP | 03-056254 | 2/2003 |
| 2008/0135576 A1* | 6/2008 | Bacon .............................. 222/36 | WO | WO 92/07599 | 5/1992 |
| 2008/0142469 A1* | 6/2008 | Zeligson ...................... 215/217 | WO | WO 92/07600 | 5/1992 |
| 2010/0059525 A1* | 3/2010 | Smith et al. ................. 220/523 | WO | WO 92/09323 | 6/1992 |
| | | | WO | WO 92/10229 | 6/1992 |
| FOREIGN PATENT DOCUMENTS | | | WO | WO 93/03783 | 3/1993 |
| AU | 2003234748 | 9/2003 | WO | WO 93/24167 | 12/1993 |
| DE | 629163 | 4/1936 | WO | WO 94/05359 | 3/1994 |
| DE | 3324699 | 12/1984 | WO | WO 94/19042 | 9/1994 |
| DE | 8715223 | 2/1988 | WO | WO 95/08484 | 3/1995 |
| DE | 3734894 | 3/1992 | WO | WO 96/39337 | 12/1996 |
| DE | 4111895 | 10/1992 | WO | WO 98/00770 | 1/1998 |
| DE | 19745513 | 4/1999 | WO | WO 98/41254 | 9/1998 |
| DE | 29818662 | 3/2000 | WO | WO 98/52634 | 11/1998 |
| DE | 10061723 | 7/2002 | WO | WO 99/25407 | 5/1999 |
| EP | 0312073 | 4/1989 | WO | WO 99/36116 | 7/1999 |
| EP | 0373753 | 6/1990 | WO | WO 99/64095 | 12/1999 |
| EP | 0414536 | 2/1991 | WO | WO 00/01436 | 1/2000 |
| EP | 0428380 | 5/1991 | WO | WO 00/16836 | 3/2000 |
| EP | 0448204 | 9/1991 | WO | WO 00/59806 | 10/2000 |
| EP | 0501365 | 9/1992 | WO | WO 01/31578 | 5/2001 |
| EP | 0629563 | 12/1994 | WO | WO 01/32247 | 5/2001 |
| EP | 0684047 | 11/1995 | WO | WO 01/37909 | 5/2001 |
| EP | 0764312 | 4/1998 | WO | WO 0137909 A1 * | 5/2001 |
| EP | 1104318 | 8/1999 | WO | WO 02/11802 | 2/2002 |
| EP | 1003583 | 5/2000 | WO | WO 02/38207 | 5/2002 |
| EP | 1019125 | 7/2000 | WO | WO 02/43794 | 6/2002 |
| EP | 0883415 | 5/2002 | WO | WO 02/45783 | 6/2002 |
| EP | 1229953 | 8/2002 | WO | WO 02/053295 | 7/2002 |
| EP | 1254678 | 11/2002 | WO | WO 02/058771 | 8/2002 |
| EP | 1267970 | 1/2003 | WO | WO 02/058772 | 8/2002 |
| EP | 1267975 | 1/2003 | WO | WO 03/010154 | 2/2003 |
| EP | 1298065 | 4/2003 | WO | WO 03/012565 | 2/2003 |
| FR | 2204766 | 5/1974 | WO | WO 03/055548 | 7/2003 |
| FR | 2471535 | 6/1981 | WO | WO 03/080161 | 10/2003 |
| FR | 2483262 | 12/1981 | WO | WO 03/086518 | 10/2003 |
| FR | 2654627 | 5/1991 | WO | WO 2004/041670 | 11/2003 |
| FR | 2660630 | 10/1991 | WO | WO 03/101514 | 12/2003 |
| FR | 2701653 | 8/1994 | WO | WO 2004/022142 | 3/2004 |
| GB | 161969 | 7/1922 | WO | WO 2004/022143 | 3/2004 |
| GB | 727195 | 3/1955 | WO | WO 2004/022242 | 3/2004 |
| GB | 939324 | 10/1963 | WO | WO 2004/028608 | 4/2004 |
| GB | 997617 | 7/1965 | WO | WO 2004/041339 | 5/2004 |
| GB | 1012565 | 12/1965 | WO | WO 2004/078236 | 9/2004 |
| GB | 1269811 | 4/1972 | | | |
| GB | 1403826 | 8/1975 | * cited by examiner | | |

DISPENSER AND COUNTER

CROSS REFERENCE TO RELATED APPLICATIONS

This application is for entry into the U.S. national phase under §371 for International Application No. PCT/GB04/005165 having an international filing date of Dec. 10, 2004, and from which priority is claimed under all applicable sections of Title 35 of the United States Code including, but not limited to, Sections 120, 363 and 365(c), and which in turn claims priority to United Kingdom patent application 0328859.4 filed on Dec. 12, 2003.

Technical Field

The present invention relates to a dispenser for dispensing a substance in individual portions counted by a counter.

BACKGROUND OF THE INVENTION

The invention is applicable to dispensers for dispensing portions of the substances in solid, liquid or gaseous form or mixtures thereof. It has particular application for dispensing aerosol propelled gaseous, gas borne or droplet substances. The first of the embodiments described below are for this application. Other embodiments are for dispensing liquids and pills.

I have applied for a number of patents on dispensers for a gaseous, gas borne or droplet substance. In particular, in my prior International Patent Application, PCT/GB98/00770, at least as amended on entry in the European Regional Phase, there is described and claimed:

A dispenser for a gaseous, gas borne or droplet substance, the dispenser including:
  a body having a mouthpiece with an inhalation/insufflation orifice at its end;
  a junction in the body for a source of gas or evaporable liquid comprising or containing the said substance (the source being carried by the body); and
  a breath actuatable valve, for controlling the release of said gas or liquid, comprising:
  a valve inlet connected to the junction;
  a valve outlet;
  a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
  a movable member, for moving the movable portion of the tube to control its kinking, and being movably mounted in the body for movement by the act of inhalation from a rest position towards the orifice—or at least in the direction of air flow through the dispenser;
  the tube being kinked to an obturating extent when the movable member is in a rest position and un-kinked when the movable member is moved on inhalation for release of the gas or liquid.

Such a dispenser can loosely be classed as a breath actuated, kink valve dispenser and is referred to herein as "My Earlier Breath Actuated, Kink Valve Dispenser".

With such a dispenser, in common with others of my design and other designs, there is advantage to the user in knowing how many doses are left in the reservoir of the substance source, the reservoir typically being an aerosol valve can, the can being an aluminum forging.

Two approaches to dose measurement are known.

Firstly, dispensers actuated by depression of the end of the can towards the body of the dispenser body can be provided with electronic counters which sense the number of depressions and count down to indicate exhaustion of the dispenser. This approach is costly.

A second approach is to provide the source with a transparent reservoir, typically of glass. Existing glass reservoirs have replicated the shape of the prior forged aluminum can. Their shape renders difficult estimation of the number of doses remaining.

SUMMARY OF THE INVENTION

With the object of improving My Earlier Breath Actuated, Kink Valve Dispenser, I have provided it with a counter receptacle, and made the counter removable from an exhausted dispenser for use with a new dispenser.

Such an arrangement has advantage in the ability of the relatively expensive counter to be re-used with successive dispensers. However, I believe that the following important consideration needs to be addressed:

The counter should be able to be fitted only to a dispenser that is new and unused. Failure to ensure this could result in a counter being fitted late to a partially used dispenser, with the result that the dispenser becomes, empty and/or reaches a state of variable dosage when approaching emptiness, before the counter indicates this state. In other words the counter could indicate that there are an appreciable number of doses left when the dispenser is exhausted.

In addressing this consideration, I have invented a dispenser and counter combination which is applicable more widely than aerosol propelled dispensers.

Thus, according to a first aspect of the invention there is provided a dispenser for dispensing a substance in individual portions counted by a multi-use counter having a display incremented or decremented with the count of portions dispensed and a dispense action detector for detection of portion dispensing, the dispenser comprising:
  a body having a dispensing orifice;
  a container for the substance, the container being integral with or accommodated on the body;
  a mechanism in the body and/or the container for dispensing individual portions of the substance to the orifice, the mechanism having:
    a displaceable element for initiating the dispensing action;
  an accommodation on the body for the counter with its detector arranged for detection of dispensing actions of the mechanism; and
  a closure adapted to co-operate with a portion of the body providing the accommodation for removably enclosing the counter in the accommodation.

Preferably the closure is tamper-evident.

The dispenser will normally be arranged such that the dispensing mechanism is disabled in the absence of a counter enclosed by the closure.

Normally, the closure will provide:
  an abutment for the counter to maintain the said arrangement of the detector only whilst the counter is enclosed by the closure.

There are a number of possibilities for arranging the closure on the body, in particular:

1. the closure can be irremovably connected to the body and provided with a frangible portion through which the counter can be removed; and/or
2. the closure can be provided with a frangible portion removal of which enables removal of the closure and of the counter; and/or
3. the portion of the body with which the closure co-operates can have a frangible portion for release of the counter; and/or
4. the closure can be a plug fitted into the end of the receptacle to captivate the counter; and/or
5. the closure can be a cap over the end of the receptacle to captivate the counter; and/or
6. the closure can have a window for viewing the display of the counter.

Where the dispenser is for dispensing a gaseous, gas borne or droplet substance:
  the dispensing orifice is a mouthpiece with an inhalation/insufflation orifice at its end;
  the container is a source of the substance accommodated on the body;
  the body has a junction for receiving the substance from the source;
  the source and the junction are arranged to be movable towards each other for release of a substance dose from the source to the junction;
  the dispensing mechanism is a valve provided in the source and/or downstream thereof, for releasing the substance to the mouthpiece a dose at a time;
  the displaceable member is a spout on source, displaceable inwards of the source for release of the dose therethrough to the junction.

Normally:
  the accommodation for the counter is a receptacle at the end of the source remote from the spout;
  the body has a cylindrical sidewall extending to the region of the end of the source; and
  the end of the sidewall is adapted to co-operate with the closure.

In certain embodiments, the dispenser is breath-actuated, with the counter providing an abutment for the source, at least where the counter is force actuated, and the junction being movable in the body towards the source.

Where the dispenser is adapted to be operated by manual pressure, a number of alternative arrangements are possible:
1. the dispenser can be adapted to be actuated by manual pressure on and movement of the source towards the junction, with the junction being movable in the body towards the counter and the closure; or
2. the dispenser can be adapted to be actuated by manual pressure on and movement of the junction towards the source, with the junction member being movable in the body towards the source; or
3. the dispenser can be adapted to be actuated by manual pressure on the counter and movement of the source towards the junction, with the closure being arranged to provide:
  both an abutment for the counter between actuations and manual access to the counter for depression of both it and the junction member towards the junction;
  the junction member is fixed in the body.
4. the dispenser can be adapted to be actuated by manual pressure on the counter and movement of the junction towards the source, with the closure being arranged to provide:
  both an abutment for the counter between actuations and manual access to the counter for depression of both it and the junction member towards the junction;
  the junction member is movable in the body towards the source.

The source can be a metered or non-metered dose source. At least when the dispenser is breath-actuated, an additional valve is likely provided down-stream of the source, for dose release and possibly for metering, as in My Earlier Breath Actuated, Kink Valve Dispenser.

The counter will normally have a probe in contact with the source and can be is arranged to detect removal of the source from the dispenser and to reset the counter for new use in another dispenser. Further, the counter can be:
1. a force actuated counter, acting as an abutment for the source; or incorporate
2. a displacement transducer arranged to detect a small movement of the source between its position in which the junction is moved towards it for dose release and its quiescent position or vice versa; or
3. an acoustic transducer for detecting dose release by a distinctive sound of the release.

Alternatively to the source being an aerosol device, it may be for dispensing doses of solid material, in particular doses in pill form, with
  the dispensing orifice being an opening in the body;
  the container being a compartment slidably carried in the body;
  the dispensing mechanism being
    a neck of the compartment for aligning pills to be dispensed one at a time with movement of the neck outwards of the body and includes
    a spring for biasing the neck inwards of the body; and
  the accommodation being a receptacle in the body for the counter, the receptacle being closed by the closure.

In such as a dispenser:
1. the container can have a feature arranged to approach the counter for incrementing/decrementing the counter on dispensing movement of the container;
2. the feature can be the spring;
3. the spring can abut the counter for return movement of the container after a dispensing action;
4. an interlock can be provided for preventing extension of the neck without removal of an interlock stop.

The counter for a dispenser of the invention will normally have
  a display for indicating number of doses consumed or still available to be consumed,
  a dispense action detector and
  a reset probe activated to reset the counter on its removal from the dispenser either manually or by the action of fitting it to its accommodation on a dispenser.

According to another aspect of the invention, there is provided a method of making a dispenser for dispensing a gaseous, gas borne or droplet substance in individual portions counted by a multi-use counter having a display incremented or decremented with the count of portions dispensed and a dispense action detector for detection of portion dispensing, the dispenser having:
  a main part of the body and
  an adjustable part of the body which encircles the source, is adapted to receive the closure and is adjustable longitudinally of the source to compensate for source-length tolerance,
the method including the steps of:
  assembling the source to the main part of the body within the adjustable part;

adjusting the adjustable part to compensate for the said tolerance; and fixing the adjustable part to the main part in its adjusted position.

Preferably, the adjustment step is performed by:

fitting a dummy closure to the adjustable part, whereby the dummy closure replicates the abutment to be provided in the dispenser for the source by the counter fitted against the abutment provided by the counter;

setting the mechanism to its position in which the spout is urged inwards for dose dispensing;

moving the dummy closure, adjustable body part and source inwards until a dose is released; and fixing the adjustable part in this position.

Where the closure provides an abutment for the source or the junction, removal of the counter leaves the dispenser still usable. This may be acceptable in certain circumstances as an emergency reserve. Where the counter provides the abutment, removal of it renders the dispenser no longer usable. This provides that when the dispenser is indicating via the counter that it is exhausted (in practice to the extent that correct dosage can no longer be relied upon), removal of the counter to a fresh dispenser prevents unreliable use of the dispenser.

The dispenser will normally be able to be used without a counter, either in the case the body having an abutment by fitting a cap over the receptacle with the counter or in the case of a body without an abutment by fitting a spacer simulating the counter.

Where the dispenser is for dispensing doses in pill form, a variety of simple mechanisms are known and readily adapted as described below for use with the invention. Equally, the same is true of liquid dispensers.

To help understanding of the invention, various specific embodiments thereof will now be described by way of example and with reference to the accompanying drawings, in which.

DETAILED DESCRIPTION

Referring to FIGS. 1 to 4, the dispenser there shown has a body 1, with a mouthpiece cover 2, as described in one of my recent International Patent Applications, i.e. No. PCT/GB01/03313. Opening of the cover urges a junction member 3 towards a source 4 of a medicament to be released as a dose by pressing a spout 5 of the source inwards of the source, as is well known in the art. The dose released by the source is retained in the manner of My Earlier Breath Actuated, Kink Valve Dispenser, until inhalation through the mouthpiece by the user.

The source is supported by a cap 11 clipped to the end of a source-enclosing barrel 12 with internal splines 10. For this the cap has a splined 13 abutment bush 14 received in the barrel at a determined distance D from the end of the barrel. The barrel is welded 15 to the main part 16 of the body at a position determined by the extension of the source towards the distal end 17 of the barrel when the cover is open, the welding position being determined by a plug 18 simulating the cap and its bush. Such welding is described in more detail in another of my recent International Patent Applications, i.e. No. PCT/GB03/001102.

Close to the distal end of the barrel, it has a groove 19. The cap has a collar 21 with a lip 22 for engaging in the groove 19. It also as an end disc 23 connecting the bush and the collar and having a central aperture 24 for viewing a display of an electronic counter 25. A central portion 32 of the end disc 23 is frangible with a tear groove 26.

In use the counter 25 is received in the cavity 28 formed by the bush 14 and the disc 23, with a can probe 29 in contact with the end 30 of the can. The counter has an acoustic sensor associated with the probe and firmware programmed to recognize the distinctive sound of release of a dose. On such recognition, the display 31 of the counter, visible through the aperture 24, decrements one in the count of doses left available to the user of the dispenser.

On supply of the dispenser and the counter to the user, the counter and the cap are not fitted to the dispenser. The probe is not depressed inwards of the counter, thus the counter is in quiescent state. Fitting of the counter to the recess and the cap to the dispenser brings the probe into firm contact with the can. The counter is initialized and its display shows the full count of doses in the can for example 100. Actuation of the cover 2 releases a dose to the breath actuatable valve, this dispenser being breath actuated. As use continues, the count of available doses falls until it reaches zero. The dispenser is exhausted, or at least has reached a remaining quantity of medicament such that dosage is no longer reliable. A rectangular spigot 6 is provided on the base of the body with a size and shape to irrationally fit the counter viewing aperture 24. The spigot of a fresh dispenser is engaged in the window of the exhausted dispenser. The splines 10,13 of the body barrel and the cap having irrationally engaged these members on fitting of the cap, twisting of the two dispensers with respect to each other severs the disc 23 from the rest of the cap. The counter can then be removed. Its probe 29 is no longer depressed and the counter returns to its quiescent mode, until fitted to the new dispenser. The old dispenser can still be used, if this is safe in view of the uncertainty of the dose, as an emergency reserve, with the abutment for the source on the bush 14 still being available.

Figure 1:
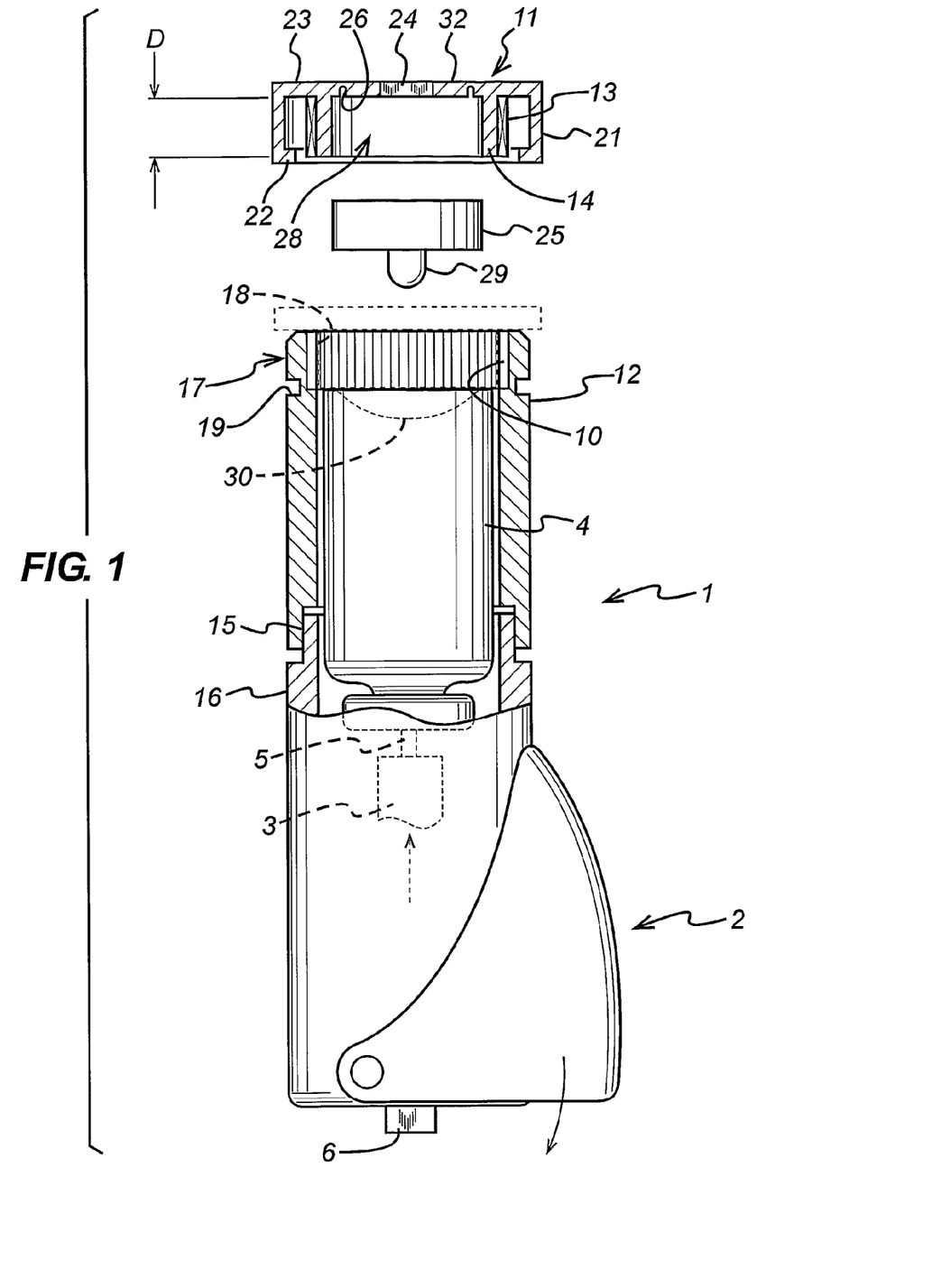
FIG. 1 is an exploded, part sectioned side view of a first dispenser of the invention.
Figure 2:
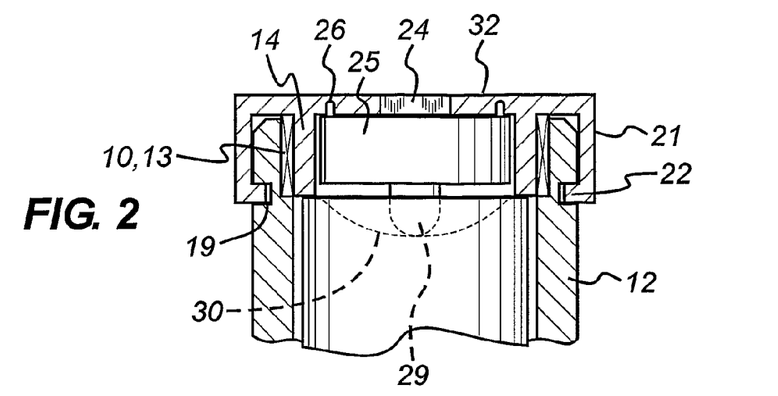
FIG. 2 is a scrap, sectional side view of the distal end of the body of the dispenser of FIG. 1.
Figure 3:
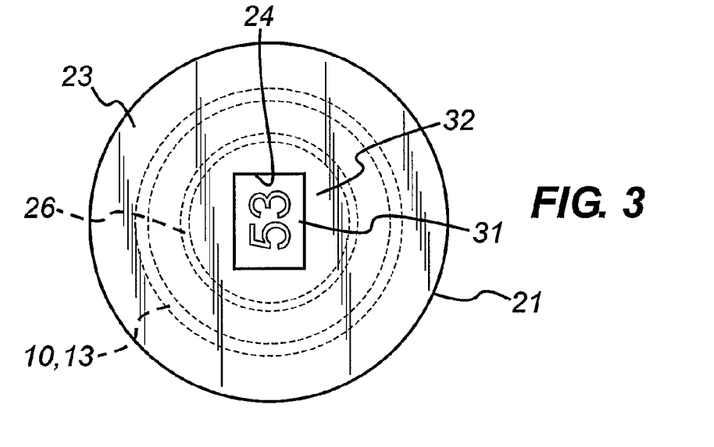
FIG. 3 is a similar, non-sectioned end view of the distal end.
Figure 4:
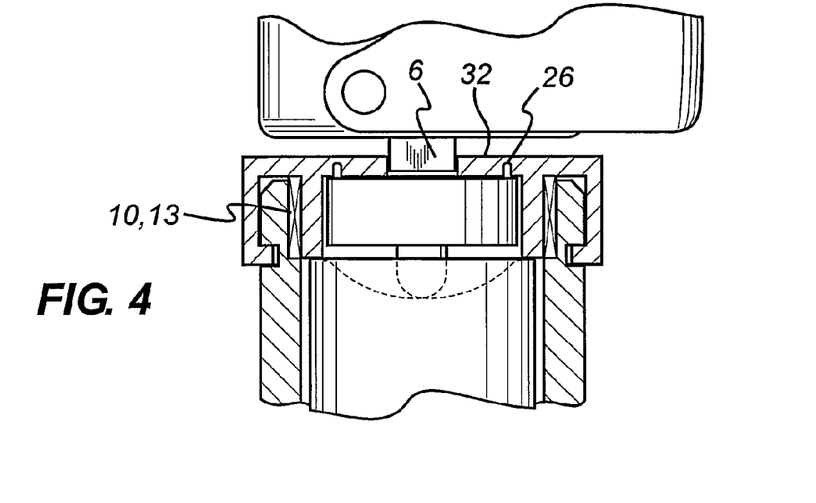
FIG. 4 is a cross-sectional side view of the distal end.
Figure 5:
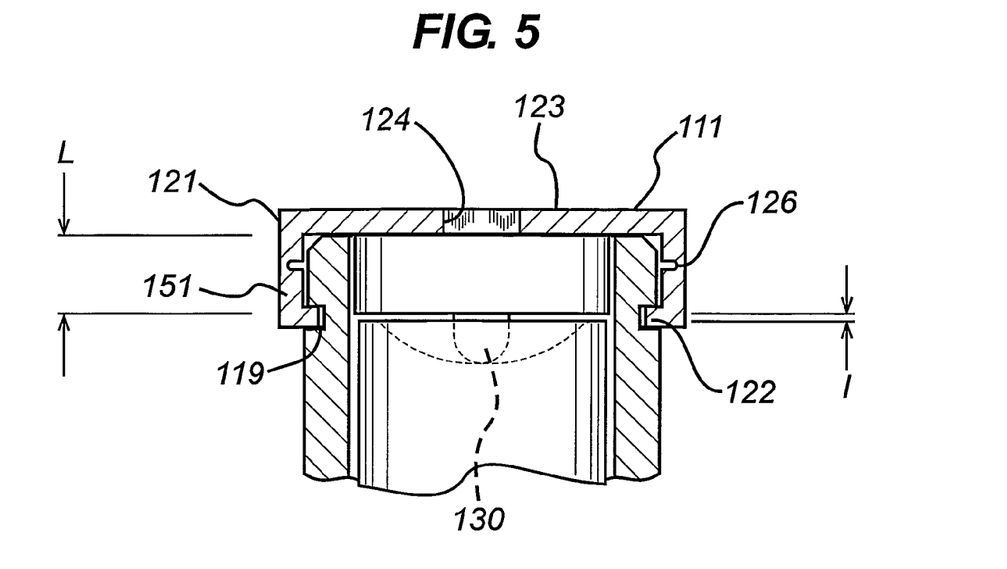
FIG. 5 is a view similar to FIG. 2 of a dispenser with a variant.
Figure 6:
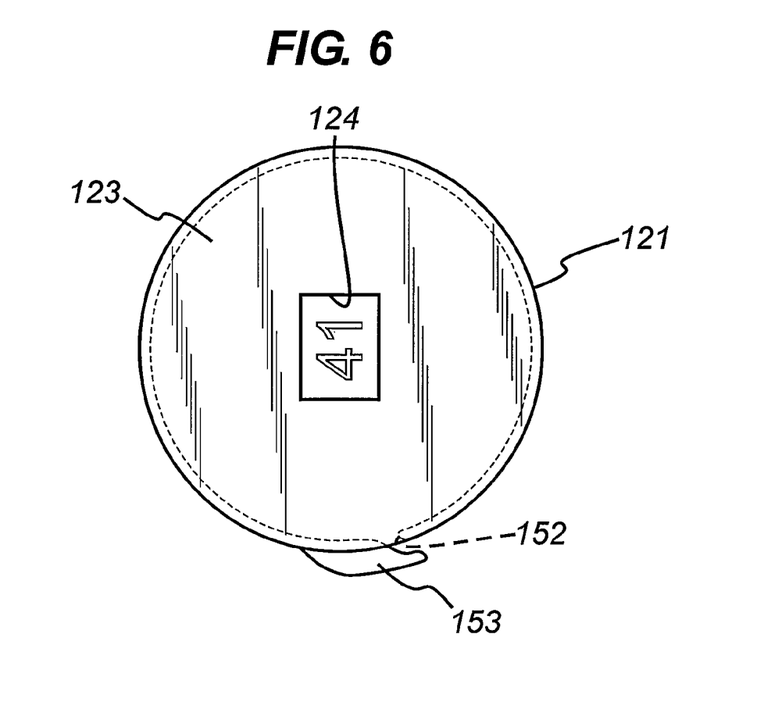
FIG. 6 is an end view of the variant of FIG. 5.

In the variant shown in FIGS. 5 & 6, the cap 111 does not have a bush against which the end of the source abuts. Rather, it is the counter against which the source abuts, but with a small free movement 1. This will be explained further in the next paragraph. The cap is closed with an end disc 123 having a window 124 through which the count of the counter is visible. Again the cap is secured by a collar 121 with a lip 122 engaging in a groove 119 in the barrel of the body. Internally, the collar is provided at mid-height with a tear groove 126.

The lower, tearable portion 151 of the collar has peripheral discontinuity 152 and a graspable protrusion 153 continuous with the tearable portion on its side opposite from the discontinuity.

In manufacture, the barrel is set on the body such that the source releases a dose when the end of the source is at a distance L, the thickness of the counter, from the end of the barrel. The throw of the cam mechanism (not shown) in the dispenser for moving the junction member towards the source is greater than the stroke of the spout into the source, so that in the quiescent state of the dispenser, a spring (not shown) in the counter urging its probe 130 towards the source returns the source to be separated from the counter by the distance 1. The counter counts on depression of the probe through this distance 1 on operation of the cam mechanism. Further it has another probe position, farther extended from the counter body in which it resets to its quiescent state.

For initial use, the counter is inserted in the end of the barrel and the cap is placed over the counter, clipping onto the barrel via the lip 122 and the groove 119. The probe is moved towards the body of the counter by contact with the source, resetting the counter from its quiescent state to the full count of doses. Use of the dispenser moves the source up through the displacement 1, with the count decrementing one dose on each use. On exhaustion of the source, the tear strip 151 is torn off, allowing the counter to be removed to a fresh dispenser. The old dispenser can still be used in an emergency, by manual pressure on the end of the source.

In a further non-illustrated variant, the counter has an integral load cell, for detecting release by detecting the force applied from the source to the counter on dispensing of a dose from the source. The force is that necessary to displace the spout inwards of the can. The counter still retains its probe as a detector of whether it is installed in a dispenser or not, i.e. whether it is in a quiescent or counting mode.

Figure 7:
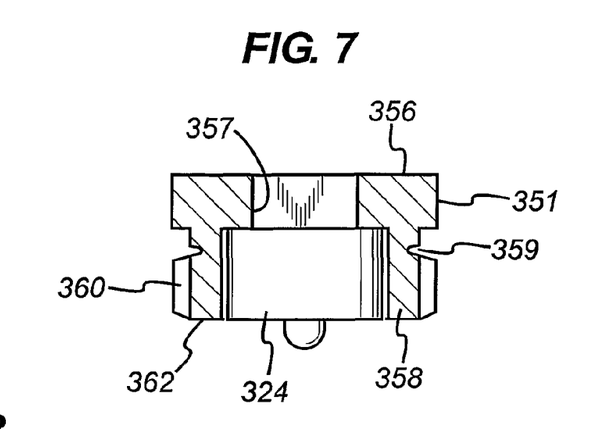
FIG. 7 is a sectional side view of a barrel plug for a second embodiment of the dispenser of the invention.
Figure 8:
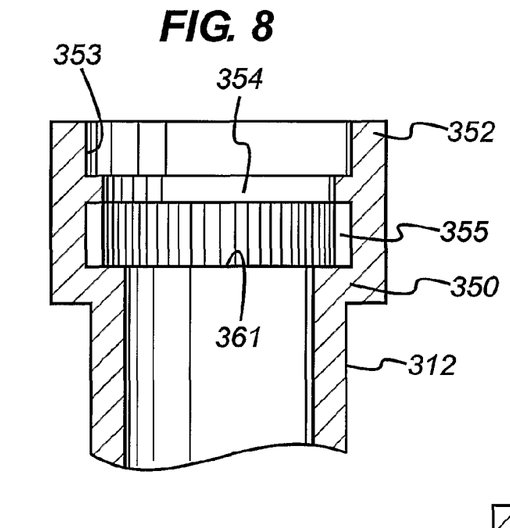
FIG. 8 is a sectional view of a distal end of the barrel of the dispenser of FIG. 7.
Figure 9:
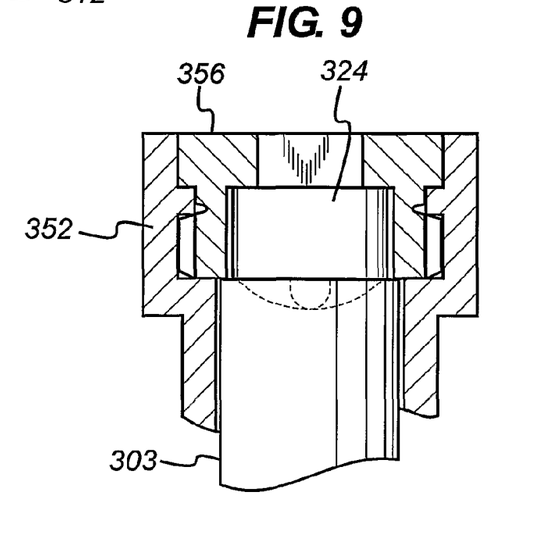
FIG. 9 is a similar view of the plug and a counter fitted to the distal end.

Turning on to the embodiment of FIGS. 7, 8 & 9, the end of the barrel 312 has step 350 out in diameter to accommodate an end plug 351 as opposed an end cap of the other embodiment and variants. The enlarged portion 352 of the barrel has a plain bore orifice 353, an annular lip 354 and a longitudinally splined length 355 between the step 350 and the lip 354. An end disc 356 of the plug has a rectangular aperture 357 for viewing a counter 324 accommodated within a sleeve 358 of the plug. Adjacent the end disc, the sleeve has a tear groove 359, beyond which complementary splines 360 extend to the end of the plug. It should be noted that the sleeve is thicker radially than the radial dimension of the step.

The barrel is set with the internal end face 361 of the step level with the end of the can 303 in its valve depressed, dose-release position. When the plug is inserted into the barrel, with a counter accommodated in it, the splines 355,360 inter-engage with the end of the splines on the plug fitting under the lip 354 and end face 362 of the sleeve 358 abutting the step face 361. The can abuts against the plug, end face 362, level with the barrel end face 361.

The counter counts as in the variant of the previous embodiment shown in FIGS. 5 & 6, i.e. by displacement of its probe. When the dispenser is exhausted, a complementary formation (not shown) on the bottom of a fresh dispenser is engaged in the rectangular aperture 357 and twisted. Twisting of the plug is resisted by the spline and the sleeve tears at the groove 359. The end disc and the counter can then be removed, and the counter fitted to the fresh dispenser with a fresh end plug.

Figure 10:
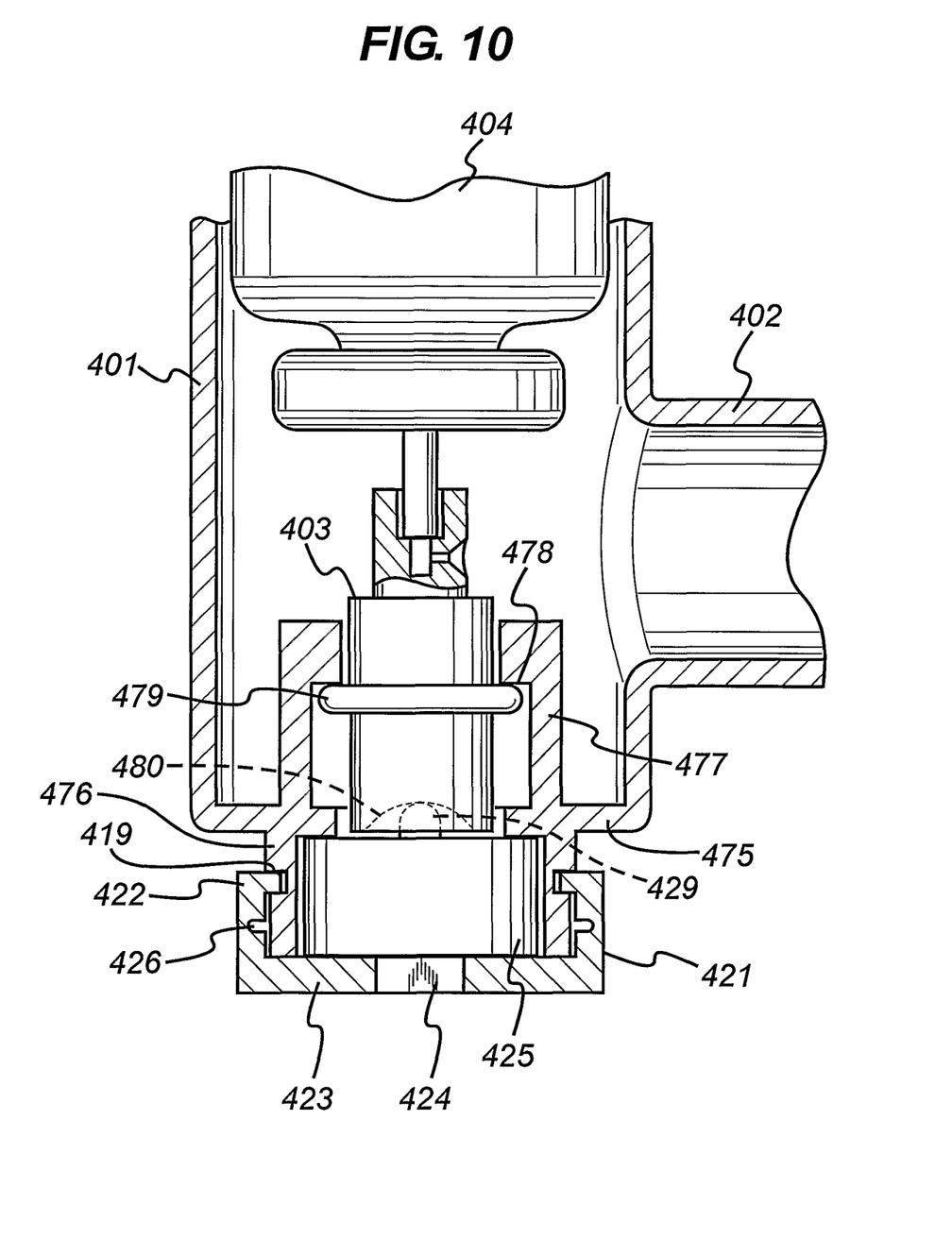
FIG. 10 is a view similar to FIG. 1 of a third dispenser of the invention.

Turning on to the embodiment of FIG. 10, the dispenser comprises a body 401, with a mouthpiece 402 and a junction member 403 for a medicament source 404. The body has a base 475, with a depending annulus 476 and an upstanding internal tube 477 for slidingly accommodating the junction, which is retained by a lip 478 on the inside of the tube and engages with a collar 479 to prevent the junction member being removed from the dispenser in the direction of the source 404. The junction member and the internal tube are of complementary shape, typically rectangular, to ensure that the nozzle on the junction member remains directed out of the mouthpiece 402.

A counter 425 is retained within the annulus 476 by an end disc 423 with a counter window 424. The end disc is held on by an integral collar 421 with a lip 422 engaging in a grove 419. The end disc is removable by severing along a groove 426 with a non-shown grippable member. These features are essentially as in the previous embodiment.

The junction member has a recess 480 for a probe 429 of the counter. The counter counts in the manner of the other embodiments and can be moved to a fresh counter in like manner. Before a counter is fitted and after it is removed, the dispenser cannot be used as the junction is not fixed to resist depression of the source and cause the spigot to be moved inwards of the source. Depression of the source is by manual pressure on the end (not shown in FIG. 10) of the source remote from its spout.

The embodiments of FIGS. 1 to 9 involve movement of the source upwards by action on the junction member on the spout, with the end of source abutting the counter or the closure. This is shown diagrammatically in FIG. 11.

The embodiment of FIG. 10 involves movement of the source downwards, in an essentially conventional manner, against the junction member, supported by the counter which is unconventional. This is shown in FIG. 12.

Figure 12:
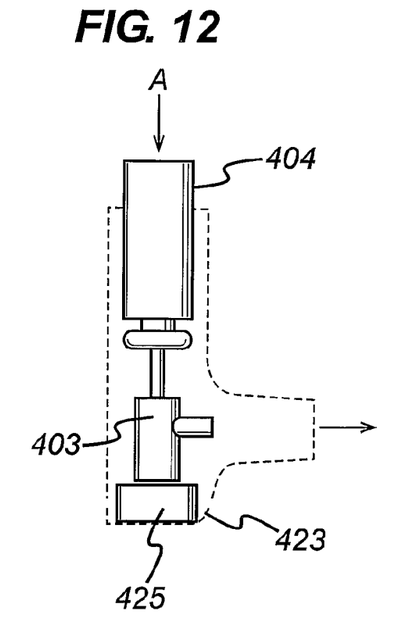
FIG. 12 is a similar depiction of the embodiment of FIG. 10.
Figure 13:
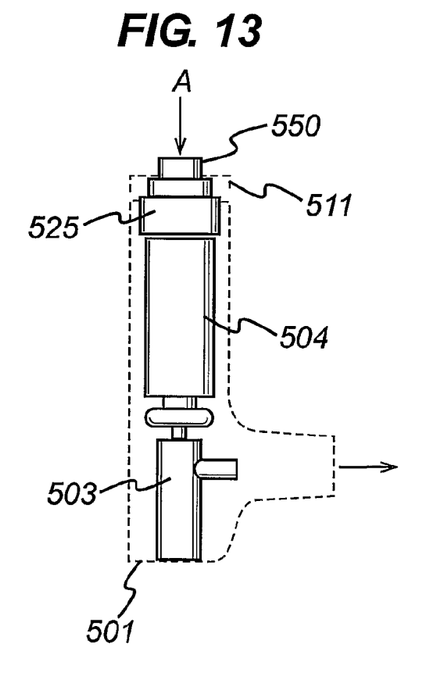
FIG. 13 is a similar depiction of another embodiment—not otherwise illustrated.
Figure 14:
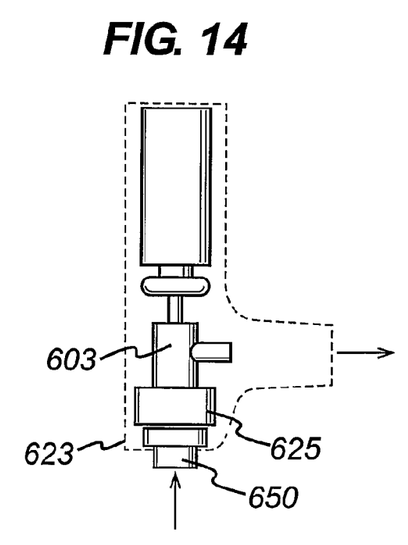
FIG. 14 is a fourth depiction of a fourth embodiment.

Two alternatives are shown diagrammatically in FIGS. 13 and 14. These involve the counter being in the positions of FIGS. 11 and 12, but the opposite ends of the sources being fixed. Manual pressure for actuation is via the counters.

Figure 11:
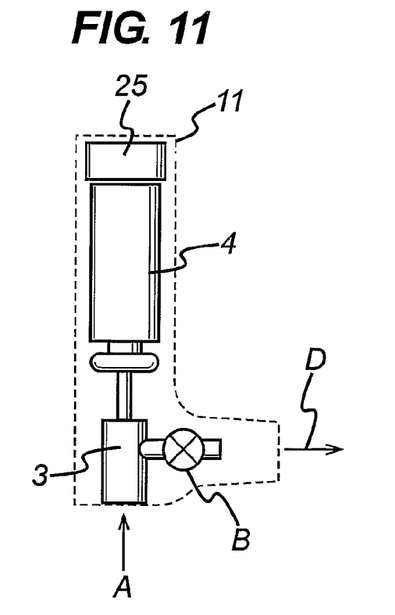
FIG. 11 is a diagrammatic depiction of the first embodiment.

In more detail, the actuation in the direction of arrow A in FIG. 11 is provided by cocking of the breath actuation mechanism B. It acts via the junction member 3 below the source 4, which has the counter 25 enclosed by the closure 11 above it. Dispensing is in the direction of arrow D.

In FIG. 12, actuation A is by manual pressure directly on to the top of the source 404, whilst the junction member 403 is supported from below via the counter 425, itself held in place by the closure 423.

In FIG. 13, actuation A is again from above via a transparent (for counter viewing) button 550, slidably retained by the closure 511 and acting on the counter 525 and hence on the source 504. The junction 503 is fast with the body 501 of the dispenser.

In FIG. 14, actuation A is from below on a button 650 acting on the counter 625 and the junction member 603. The closure 623 retains the button and the counter.

Thus it can be seen that the counter can be at either end and the actuation can be at either end. All these alternatives retain the inventive feature of the counter being retained by a closure, which is removable for removal of the counter to a fresh dispenser once the first source is exhausted.

Figure 15:
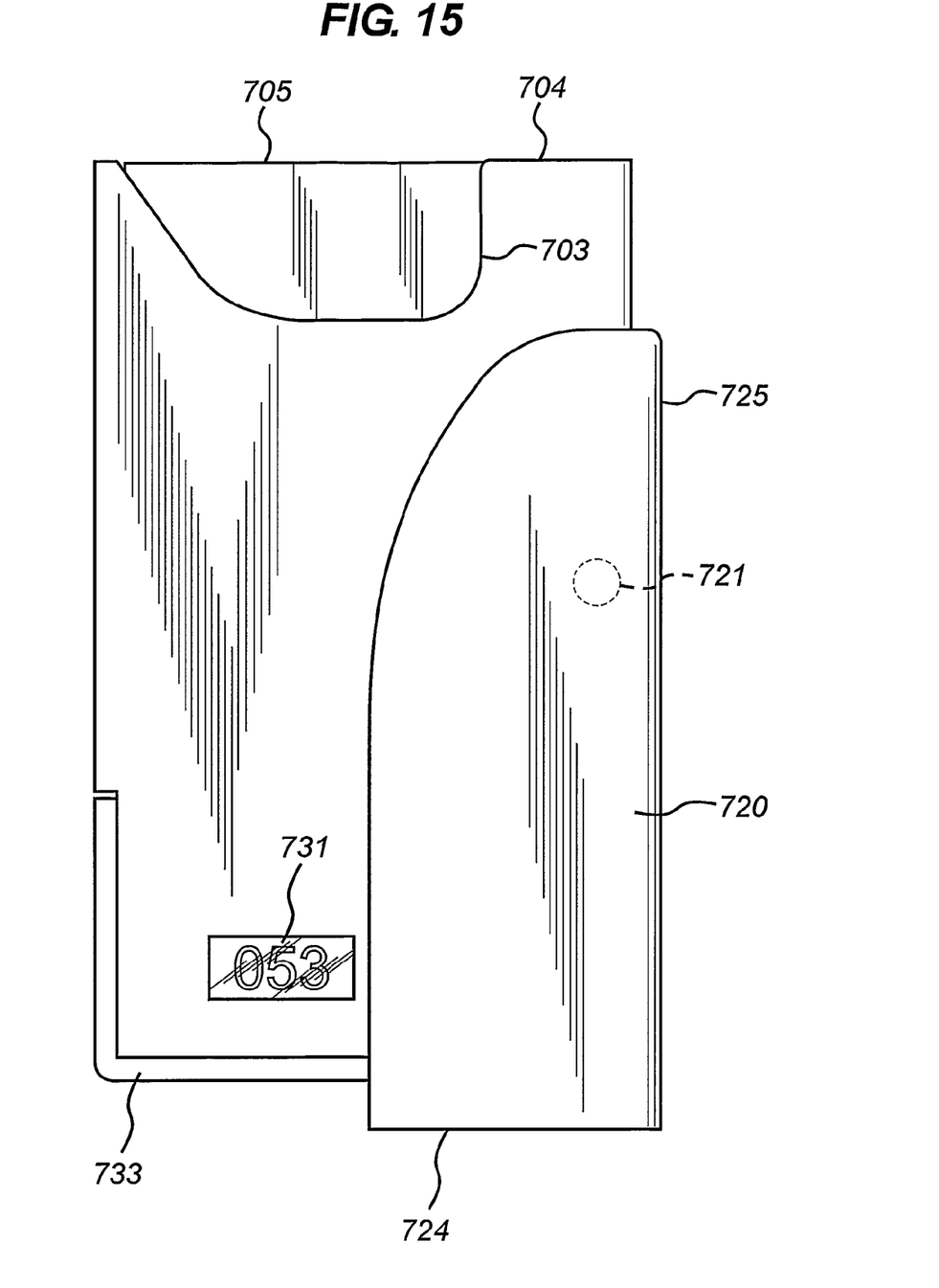
FIG. 15 is a side view of a pill dispenser of the invention.
Figure 16:
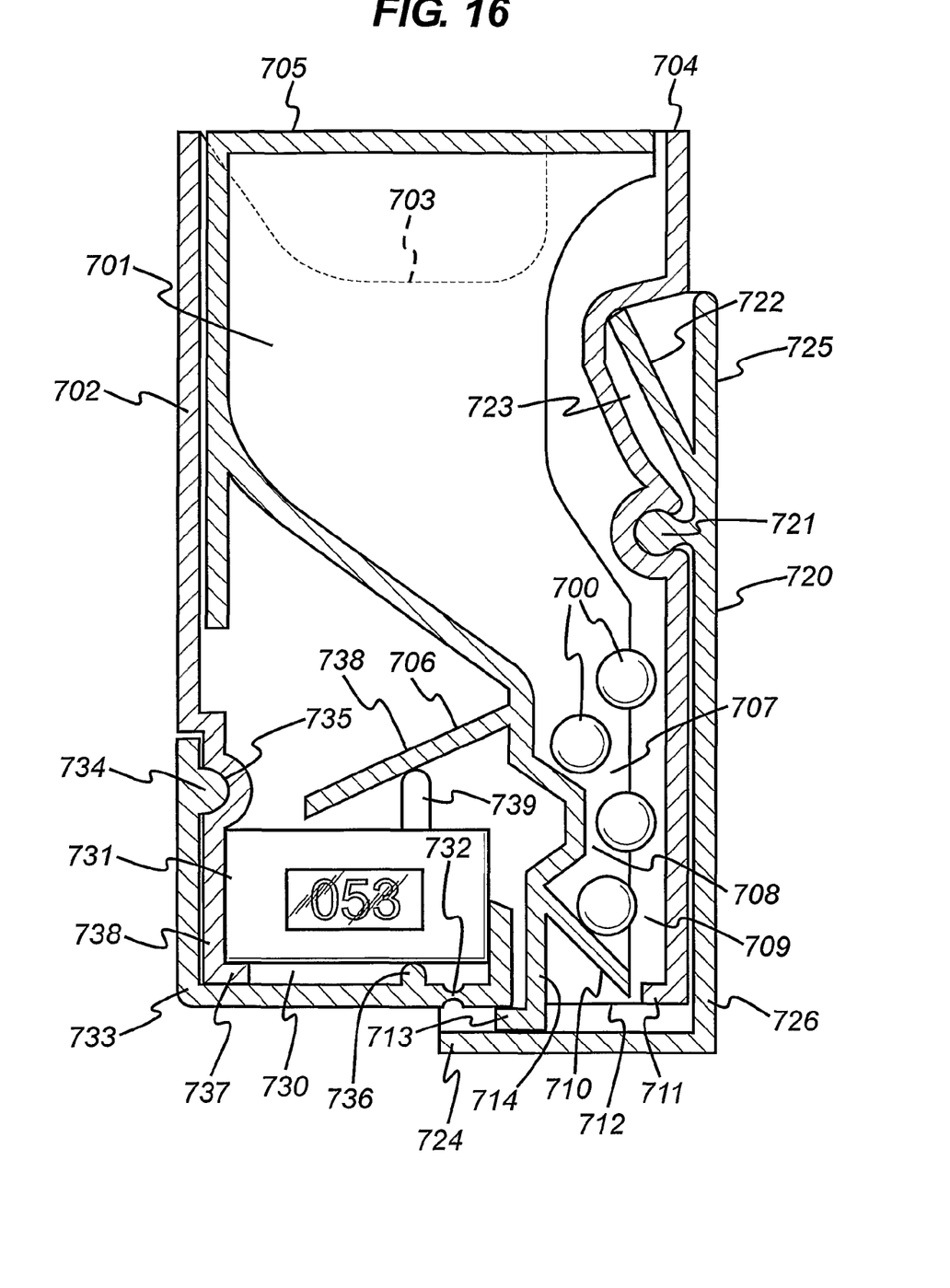
FIG. 16 is a similar cross-sectional side view of the pill dispenser.

Tuning now to FIGS. 15 & 16, the dispenser there shown is for pills 700 contained in compartment 701 slidably arranged in a body 702, which forms a sleeve around the compartment. The sleeve is scalloped 703 at its top open end 704 and the compartment has an end 705 extending above the free edge of the scallop. A spring 706 moulded integrally with the compartment biases the compartment towards the body's end 704. The compartment has a lower neck 707 with a constriction 708, which co-operates with a side of the body to define a passage 709 for the pills one at a time. One pill can fall below the constriction and comes to rest on a ramp 710 in the neck. A transverse body lip 711 co-operates with the constriction to limit the pill at the constriction from passing it when the neck is depressed to allow the bottom pill out of the dispenser via a bottom orifice 712 when the compartment's end is pressed inwards of the body. On release of the end, the spring lifts the compartment again to an extent limited by a lip 713 on a leg 714 in extending below the ramp.

Since the dispenser is for pills, it is provided with an interlock in the form of a lever 720 pivoted 721 to the side of the body sleeve. It has an integral spring 722 acting in a recess 723 to urge a stop 724 beneath the orifice 712, until pressure on a lug 725 at the level of the spring and above the pivot swings a lower portion 726, including the stop 724 clear of the orifice. For dispensing use, pressure on the lug 725 and the compartment end 705 simultaneously allows dispensing of a pill. This renders the dispenser safe in the hands of young children unable to co-ordinate the two pressure actions.

In accordance with the invention, the body has a receptacle 730 for a counter 731. The receptacle is closed by a living hinge 732 connected closure 733, formed integrally with the body. It has a pip 734 engaging in an indent 735, which keep the closure closed. The counter is only partially supported on the closure by a projection 736. It is supported beneath the distal end of the spring 706 by a flange 737 at the end of the side 738 of the body beneath the indent 735.

The arrangement of the spring bearing on the counter provides that in the absence of a counter, the compartment is not sprung to its normal position for a dispensing action. The middle 738 of the spring's proximity to the counter is detected by a probe 739, whereby the counter can count dispensing actions of the dispenser.

What is claimed is:

1. A dispenser for dispensing a substance in individual portions, the dispenser comprising:
   a body having a dispensing orifice;
   a container for the substance, the container being integral with or accommodated on the body;
   a mechanism in the body and/or the container for dispensing individual portions of the substance to the dispensing orifice, the mechanism having:
   a displaceable element for initiating a dispensing action;
   a multi-use counter having a display incremented or decremented with the count of portions dispensed;
   a dispense action detector for detection of portion dispensing;
   an accommodation in the body for the multi-use counter with its detector arranged for detection of dispensing of the mechanism; and
   a closure, adapted to co-operate with a portion of the body providing the accommodation for removably enclosing the counter in the accommodation, characterized in that the closure is adapted to be irremovably connected to the body, and the closure is provided with a frangible portion through which the multi-use counter can be removed so as to make the closure tamper-evident.

2. The dispenser as claimed in claim 1, wherein the portion of the body with which the closure co-operates has a frangible portion for release of the counter.

3. The dispenser as claimed in claim 1, wherein the closure is a plug fitted into an end of the portion of the body providing the accommodation to captivate the counter.

4. The dispenser as claimed in claim 1, wherein the closure is a cap over an end of the portion of the body providing the accommodation to captivate the counter.

5. The dispenser as claimed in claim 1, wherein the closure has a window for viewing the display of the counter.

6. The dispenser as claimed in claim 1, wherein the closure provides:
   an abutment for the counter to maintain said arrangement of the detector only whilst the counter is enclosed by the closure.

7. The dispenser as claimed in claim 6, wherein the dispenser is for dispensing a gaseous, gas borne or droplet substance and
   the dispensing orifice is a mouthpiece with an inhalation/insufflation orifice at its end;
   the container is a source of the substance accommodated on the body;
   the body has a junction for receiving the substance from the source;
   the source and the junction are arranged to be movable towards each other for release of a substance dose from the source to the junction;
   the dispensing mechanism is a valve provided in the source and/or downstream thereof, for releasing the substance to the mouthpiece a dose at a time;
   the displaceable member is a spout on the source, displaceable inwards of the source for release of the dose therethrough to the junction.

8. The dispenser as claimed in claim 7, wherein:
   the accommodation for the counter is a receptacle at an end of the source remote from the spout;
   the body has a cylindrical sidewall extending to a region of the end of the source; and
   an end of the sidewall is adapted to co-operate with the closure.

9. The dispenser as claimed in claim 8, wherein:
   the dispenser is breath-actuated;
   the counter provides an abutment for the source; and
   the junction is movable in the body towards the source.

10. The dispenser as claimed in claim 8, wherein:
    the dispenser is adapted to be actuated by manual pressure on and movement of the source towards the junction; and
    the junction is movable in the body towards the counter and the closure.

11. The dispenser as claimed in claim 8, wherein:
    the dispenser is adapted to be actuated by manual pressure on and movement of the junction towards the source; and
    the junction member is movable in the body towards the source.

12. The dispenser as claimed in claim 1, wherein the dispenser is for dispensing a gaseous, gas borne or droplet substance and
    the dispensing orifice is a mouthpiece with an inhalation/insufflation orifice at its end;
    the container is a source of the substance accommodated on the body;
    the body has a junction for receiving the substance from the source;
    the source and the junction are arranged to be movable towards each other for release of a substance dose from the source to the junction;
    the dispensing mechanism is a valve provided in the source and/or downstream thereof, for releasing the substance to the mouthpiece a dose at a time;
    the displaceable member is a spout on the source, displaceable inwards of the source for release of the dose therethrough to the junction.

13. The dispenser as claimed in claim 12, wherein:
    the accommodation for the counter is a receptacle at an end of the source remote from the spout;

the body has a cylindrical sidewall extending to the region of the end of the source; and an end of the sidewall is adapted to co-operate with the closure.

14. The dispenser as claimed in claim 13, wherein:

the dispenser is adapted to be actuated by manual pressure on the counter and movement of the source towards the junction, the closure is arranged to provide:

both an abutment for the counter between actuations and manual access to the counter for depression of both it and the source towards the junction;

the junction is fixed in the body.

15. The dispenser as claimed in claim 13, wherein:

the dispenser is adapted to be actuated by manual pressure on the counter and movement of the junction towards the source, with the closure being arranged to provide:

both an abutment for the counter between actuations and manual access to the counter for depression of both it and the junction member towards the junction;

the junction member is movable in the body towards the source.

16. The dispenser as claimed in claim 1, wherein the container is a source of the substance accommodated on the body and wherein the source is a metered dose source.

17. The dispenser as claimed in claim 16, wherein the dispensing orifice is a mouthpiece with an inhalation/insufflation orifice at its end, wherein the container is a source of the substance accommodated on the body, wherein the dispensing mechanism is a value provided in the source and/or downstream thereof, for releasing the substance to the mouthpiece a dose at a time, and wherein an additional valve is provided down stream of the source.

18. The dispenser as claimed in claim 1, wherein the container is a source of the substance accommodated on the body and wherein the counter is a force actuated counter, acting as an abutment for the source.

19. The dispenser as claimed in claim 1, wherein the container is a source of the substance accommodation on the body, wherein the body has a juction for receiving the substance from the source, and wherein the counter is a displacement transducer arranged to detect a small movement of the source between its position in which the junction is moved towards it for dose release and its quiescent position or vice versa.

20. The dispenser as claimed in claim 1, wherein the counter is an acoustic transducer for detecting portion dispensing by a distinctive sound of the release.

21. The dispenser as claimed in claim 1, wherein the container is a source of the accommodated on the body and wherein the counter has a probe in contact with the source.

22. The dispenser as claimed in claim 21, wherein the probe is arranged to detect removal of the source from the dispenser and to reset the counter for new use in another dispenser.

23. The dispenser as claimed in claim 1, wherein the dispenser is for dispensing doses in pill form and the dispensing orifice is an opening in the body;

the container is a compartment slidably carried in the body;

the dispensing mechanism is a neck of the compartment for aligning pills to be dispensed one at a time with movement of the neck outwards of the body and includes a spring for biasing the neck inwards of the body; and the accommodation is a receptacle in the body for the counter, the receptacle being closed by the closure.

24. The dispenser as claimed in claim 23, wherein the container has a feature arranged to approach the counter for incrementing/decrementing the counter on dispensing movement of the container.

25. The dispenser as claimed in claim 24, wherein the feature is the spring.

26. The dispenser as claimed in claim 24, wherein the spring abuts the counter for return movement of the container after a dispensing action.

27. The dispenser as claimed in claim 23, including an interlock preventing extension of the neck without removal of an interlock stop.

28. The dispenser as claimed in claim 1, the dispensing mechanism is disabled in the absence of a counter enclosed by the closure.

29. A dispenser as claimed in claim 1, wherein the dispensing mechanism is a value provided in the source and/or downstream thereof, for releasing the substance to the mouthpiece a dose at a time, the dispenser comprising a multi-use counter comprising:

a display for indicating number of doses consumed or still available to be consumed, a dispense action detector and a reset probe activated to reset the counter on its removal from the dispenser either manually or by the action of fitting it to its accommodation on a dispenser.

30. A dispenser for dispensing a substance in individual portions, the dispenser comprising:

a body having a dispensing orifice;

a container for the substance, the container being integral with or accommodated on the body;

a mechanism in the body and/or the container for dispensing individual portions of the substance to the dispensing orifice, the mechanism having:

a displaceable element for initiating a dispensing action;

a multi-use counter having a display incremented or decremented with the count of portions dispensed;

a dispense action detector for detection of portion dispensing;

an accommodation in the body for the multi-use counter with its detector arranged for detection of dispensing of the mechanism; and a rigid closure, adapted to co-operate with a portion of the body providing the accommodation for removably enclosing the counter in the accommodation, characterised in that the rigid closure is provided with a frangible portion for release of the counter, such that the closure is tamper-evident.

31. The dispenser as claimed in claim 30, wherein the closure is a cap over an end of the portion of the body providing the accommodation to captivate the counter.

32. The dispenser as claimed in claim 30, wherein the closure has a window for viewing the display of the counter.

33. The dispenser as claimed in claim 30, wherein the closure provides:

an abutment for the counter to maintain said arrangement of the detector only whilst the counter is enclosed by the closure.

34. The dispenser as claimed in claim 33, wherein the dispenser is for dispensing a gaseous, gas borne or droplet substance and the dispensing orifice is a mouthpiece with an inhalation/insufflation orifice at its end;

the container is a source of the substance accommodated on the body;

the body has a junction for receiving the substance from the source;

the source and the junction are arranged to be movable towards each other for release of a substance dose from the source to the junction;

the dispensing mechanism is a valve provided in the source and/or downstream thereof, for releasing the substance to the mouthpiece a dose at a time;

the displaceable member is a spout on the source, displaceable inwards of the source for release of the dose therethrough to the junction.

35. The dispenser as claimed in claim 34, wherein:

the accommodation for the counter is a receptacle at an end of the source remote from the spout;

the body has a cylindrical sidewall extending to a region of the end of the source; and an end of the sidewall is adapted to co-operate with the closure.

36. A dispenser for dispensing a substance in individual portions, the dispenser comprising:

a body having a dispensing orifice;

a container for the substance, the container being integral with or accommodated on the body;

a mechanism in the body and/or the container for dispensing individual portions of the substance to the dispensing orifice, the mechanism having:

a displaceable element for initiating a dispensing action;

a multi-use counter having a display incremented or decremented with the count of portions dispensed;

a dispense action detector for detection of portion dispensing;

an accommodation in the body for the multi-use counter with its detector arranged for detection of dispensing of the mechanism; and a closure, adapted to co-operate with a portion of the body providing the accommodation for removably enclosing the counter in the accommodation, characterized in that the closure is adapted to be irremovably connected to the body, and the closure is provided with a frangible portion through which the multi-use counter can be removed so as to make the closure tamper-evident wherein the closure is a cap over an end of the portion of the body providing the accommodation to captivate the counter.

\* \* \* \* \*

UNITED STATES PATENT AND TRADEMARK OFFICE
CERTIFICATE OF CORRECTION

PATENT NO.         : 8,408,208 B2
APPLICATION NO.    : 10/582656
DATED              : April 2, 2013
INVENTOR(S)        : Raymond John Bacon Page 1 of 1

It is certified that error appears in the above-identified patent and that said Letters Patent is hereby corrected as shown below:

In the Claims:

At column 11, line 51, claim 21, line 2, insert the word --substance-- after the word "the".

Signed and Sealed this
Ninth Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,408,208 B2 | Page 1 of 1 |
| APPLICATION NO. | : 10/582656 | |
| DATED | : April 2, 2013 | |
| INVENTOR(S) | : Bacon | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1118 days.

Signed and Sealed this
Thirtieth Day of September, 2014

Michelle K. Lee
*Deputy Director of the United States Patent and Trademark Office*